United States Patent
Ernst et al.

(10) Patent No.: US 10,456,764 B2
(45) Date of Patent: Oct. 29, 2019

(54) CATALYST BED CONFIGURATION FOR OLEFIN PRODUCTION

(71) Applicant: Borealis AG, Vienna (AT)

(72) Inventors: Eberhard Ernst, Weissenfels (DE); Mariana Stoyanova, Berlin (DE); Evgeny Kondratenko, Rostock (DE); David Linke, Berlin (DE)

(73) Assignee: Borealis AG, Vienna (AT)

( * ) Notice: Subject to any disclaimer, the term of this patent is extended or adjusted under 35 U.S.C. 154(b) by 348 days.

(21) Appl. No.: 14/906,626

(22) PCT Filed: Jul. 22, 2014

(86) PCT No.: PCT/EP2014/065667
§ 371 (c)(1),
(2) Date: Jan. 21, 2016

(87) PCT Pub. No.: WO2015/011115
PCT Pub. Date: Jan. 29, 2015

(65) Prior Publication Data
US 2016/0167003 A1    Jun. 16, 2016

(30) Foreign Application Priority Data
Jul. 23, 2013 (EP) .................................... 13177610

(51) Int. Cl.
*B01J 8/04* (2006.01)
*C07C 6/04* (2006.01)
*B01J 23/30* (2006.01)

(52) U.S. Cl.
CPC ..................................... *B01J 8/04* (2013.01); *C07C 6/04* (2013.01); *B01J 23/30* (2013.01);
(Continued)

(58) Field of Classification Search
None
See application file for complete search history.

(56) References Cited

U.S. PATENT DOCUMENTS

| 3,365,513 | A | 1/1968 | Heckelsberg |
| 3,546,313 | A | 12/1970 | Banks |

(Continued)

FOREIGN PATENT DOCUMENTS

| EP | 1854776 A1 | 11/2007 |
| WO | 2006052688 A2 | 5/2006 |

OTHER PUBLICATIONS

Robert L Banks et al: "New Developments and Concepts in Enhancing Activities of Heterogeneous Metathesis Catalysts", Journal of Molecular Catalysis, Elsevier, NL, vol. 28, No. 1-3, Jan. 1, 1985 (Jan. 1, 1985), pp. 117-131, XP009136081, ISSN: 0304-5102.

*Primary Examiner* — In Suk C Bullock
*Assistant Examiner* — Ali Z Fadhel
(74) *Attorney, Agent, or Firm* — The Webb Law Firm

(57) ABSTRACT

A catalyst bed configuration, in particular for olefin conversion by metathesis, comprising at least one main catalyst bed comprising a) at least one first catalyst component comprising a metathesis catalyst, and b) at least one second catalyst component comprising a catalyst for double bond isomerization, whereby the first and second catalyst are intimate mixed with each other, and at least one catalyst pre-bed arranged upstream of the at least one main catalyst bed comprising at least one compound selected from the group of alkaline earth oxides. The mass ratio of the at least one catalyst pre-bed to the at least one main catalyst bed is between 1:2 and 2.5:1, preferably between 1:1.5 and 2.5:1, more preferably between 1:1 and 2.5:1, most preferably between 1:1 and 2:1.

16 Claims, 1 Drawing Sheet

(52) U.S. Cl.
CPC ..... *B01J 2208/025* (2013.01); *C07C 2521/08* (2013.01); *C07C 2521/10* (2013.01); *C07C 2523/30* (2013.01); *Y02P 20/52* (2015.11)

(56) References Cited

U.S. PATENT DOCUMENTS

| | | | |
|---|---|---|---|
| 3,865,751 A | | 2/1975 | Banks et al. |
| 3,915,897 A | | 10/1975 | Reusser et al. |
| 4,071,471 A | | 1/1978 | Banks et al. |
| 4,547,617 A | | 10/1985 | Welch |
| 4,575,575 A | | 3/1986 | Drake et al. |
| 5,300,718 A | | 4/1994 | McCaulley |
| 6,281,402 B1 | | 8/2001 | Coupard et al. |
| 2006/0047176 A1 | * | 3/2006 | Gartside ............... C07C 5/2506 585/643 |
| 2010/0056839 A1 | * | 3/2010 | Ramachandran ...... B01J 23/007 585/646 |
| 2010/0167911 A1 | * | 7/2010 | Shum ...................... B01J 23/92 502/51 |
| 2011/0021858 A1 | * | 1/2011 | Ramachandran ........ B01J 21/08 585/670 |

* cited by examiner

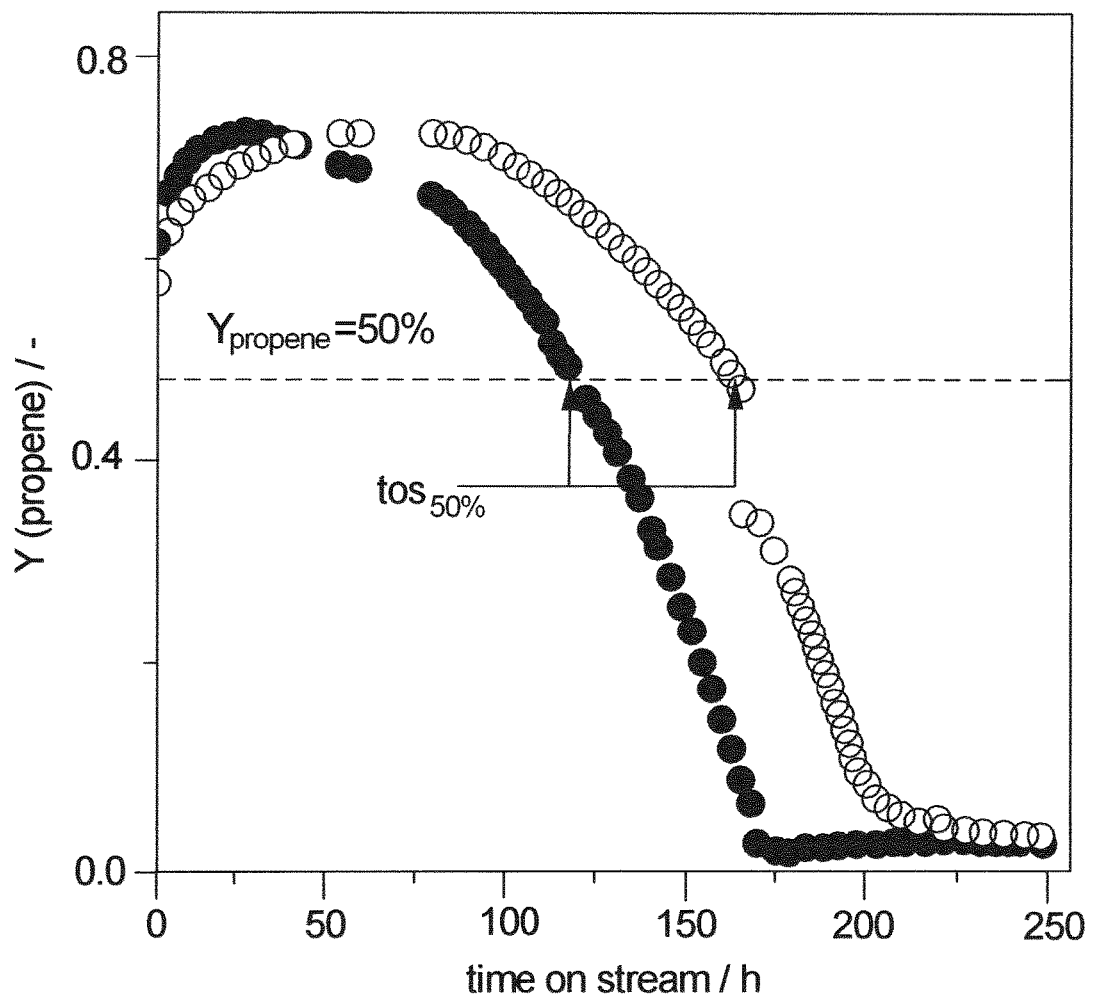

CATALYST BED CONFIGURATION FOR OLEFIN PRODUCTION

CROSS-REFERENCE TO RELATED APPLICATIONS

This application is the United States national phase of International Application No. PCT/EP2014/065667 filed Jul. 22, 2014, and claims priority to European Patent Application No. 13177610.6 filed Jul. 23, 2013, the disclosures of which are hereby incorporated in their entirety by reference.

BACKGROUND OF THE INVENTION

Field of the Invention

The present invention relates to a catalyst bed configuration, the use of said catalyst bed, a reactor comprising said catalyst bed and a process for obtaining an olefin.

Description of Related Art

Butenes are the $C_4H_8$ mono-olefin isomers such as 1-butene, cis-2-butene, trans-2-butene and iso-butene (2-methylpropene). If it is not specifically mentioned, cis-2-butene, trans-2-butene are also called as 2-butene within the frame of the present invention. The sum of cis-2-butene, trans-2-butene, and 1-butene is denoted as n-butenes. Butenes are almost always commercially produced as by-products in a petroleum refinery by cracking processes or by catalytic ethene dimerisation. Butenes can be used for multiple purposes like in the manufacture of polymers and other chemicals like insecticides, antioxidants, adhesives, sealants or elastomers.

The use of n-butenes for the production of propen has gained industrial importance in the last decades. The synthesis of propene using n-butenes as starting material is based on the metathesis reaction. Hereby, 2-butene is converted in the presence of ethene to propene according to the following overall reaction scheme:

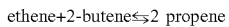

ethene+2-butene⇌2 propene

This reaction occurs typically in the presence of a catalyst comprising metal oxide of the group 6 or 7 of the periodic system of the elements (PSE). Typical active components of catalysts used for olefin metathesis are tungsten oxide supported on silica (U.S. Pat. No. 3,365,513) or rhenium oxides and molybdenum oxides supported on alumina or silica alumina (U.S. Pat. Nos. 4,547,617; 6,281,402).

Various modifications and improvements of the metathesis catalysts have been described. The physical mixing of the metathesis catalyst with an isomerisation catalyst for shifting the double bond in 1-butene to 2-butene has been proven to increase the overall production yield (U.S. Pat. Nos. 3,865,751; 3,915,897; 4,575,575). Typical double bond isomerisation catalysts include basic metal oxides as for instance magnesium oxide or calcium oxide, which can be admixed with the metathesis catalyst. The use of magnesium oxide (MgO) as a co-catalyst enables reduction of the reaction temperature to 250-300° C. from approximately 400° C. for pure silica supported tungsten oxide ($WO_3/SiO_2$). The weight ratio of magnesium oxide to $WO_3/SiO_2$ is in the range of 0.1-20. Magnesium oxide has the function to isomerise 1-butene to 2-butene since both olefins are present in technical feeds. It is important to highlight that magnesium oxide alone shows negligible metathesis activity.

Besides its ability to act as an isomerisation catalyst magnesium oxide has also been known for its ability to remove or destroy traces of contaminants from the olefin feed that are detrimental to metathesis catalysts, in particular when used as a "guard bed" (J. Mol. Cat. 1985, 28:117-131). Magnesium oxide can be for instance arranged on top of a composition comprising the metathesis catalyst and an isomerisation catalyst (US 2010/0056839 A1, US 2010/167911 A1). Here the optimal catalyst activation is combined with the guard pre-bed function to remove poisons and the isomerisation of 1-butene to 2-butene. When applying this approach a technical metathesis reactor is typically filled with a mixture of MgO and $WO_3/SiO_2$ and an MgO pre-bed upstream of the main bed.

However, the known technical metathesis catalysts for propene production suffer from a decrease in their activity with time on stream (deactivation). Coke formation is one of the origins of the catalyst deactivation. Therefore, a regeneration of the catalyst is imperative if the catalytic activity decreases below a certain level during the production cycle. The regeneration is usually performed at temperatures up to 650° C. Such high-temperature treatment additionally diminishes the lifetime of the catalyst. It is therefore highly desirable to extend the cycle time to improve the process economy through reducing the number of regeneration steps and increasing the catalyst lifetime.

SUMMARY OF THE INVENTION

It is therefore an object of this invention to provide a catalyst bed configuration which prolongs the catalyst lifetime without negative impact on activity and selectivity and thus allows for longer reactor cycles before regeneration of the catalyst is necessary.

Accordingly, a catalyst bed configuration is being provided, in particular suitable for olefin conversion by metathesis, which comprises at least one main catalyst bed comprising a) at least one first catalyst component comprising a metathesis catalyst, and b) at least one second catalyst component comprising a catalyst for double bond isomerisation, whereby the first and second catalysts are physically mixed with each other, and at least one catalyst pre-bed arranged upstream of the at least one main catalyst bed comprising at least one alkaline earth oxide. Said catalyst pre-bed is in particular located immediately upstream and/or directly on the top surface of the main catalyst bed.

The catalyst composition according to the invention is characterized by a mass ratio of the at least one catalyst pre-bed and the at least one main catalyst bed between 1:2 and 2.5:1, preferably between 1:1.5 and 2.5:1, more preferably between 1:1 and 2.5:1, most preferably between 1:1 and 2:1. The ratio can also be between 1:1 and 1.5:1. It is to be understand that the ratio of catalyst pre-bed to catalyst main bed is valid for a constant or fixed reactor volume, i.e. for a reactor having a constant length/diameter-ratio which is defined further below.

In case the mass ratio of catalyst pre-bed to the at least one main catalyst bed is between 1:2 and 2.5:1 it is to be understood that a mass ratio of 1:1.6 in case of magnesium oxide as catalyst pre-bed to a mixture of magnesium oxide and tungsten oxide on a silica carrier in a ratio of 7:1 as main catalyst bed is exempted or disclaimed from the claimed range of catalyst pre-bed/main catalyst bed. Said exempted/disclaimed ratio is disclosed in U.S. Pat. No. 3,865,751 and is used for the disproportion of pentene to olefins having a lower molecular weight; i.e. not for ethen/2-butene metathesis reaction.

The specific mass ratio between the pre-bed and the main-bed has a surprising impact on the catalytic performance. The production time of the metathesis product as for instance propene and therefore the cycle time increase dramatically with rising ratio of catalyst pre-bed to the main catalyst bed. However, if it is possible to increase the cycle time, that means the time between two regeneration steps and thus the overall catalyst lifetime can be extended.

It was found that the time-on-stream olefin conversion, such as in case of propene production, can be significantly improved when the ratio between pre-bed and main-bed is increased at a fixed volume of the whole catalyst bed (main bed plus pre-bed). This is surprising and was not to be expected since the amount of the catalytically active component such as $WO_3/SiO_2$ becomes smaller upon increasing this ratio.

In case of the catalyst bed with the ratio of the pre-bed to the main bed of 0.5 (1:2), the time to achieve the maximal product yield, such as propene yield is slightly extended, while the time period of the commercially attractive propene production is significantly extended. As a consequence, the total amount of propene produced until catalyst regeneration is increased. Upon further increasing the pre-bed/main-bed ratio to 1 (1:1), the time to achieve the maximal propene yield is again extended and the time-on-stream propene production increases and the total amount of propene produced in a given time is thus also increased. Furthermore, the effect of the improved catalyst performance is stable over many regeneration cycles. This is important for the practical applicability.

In a further embodiment the metathesis catalyst in the main catalyst bed of the present invention comprises metal oxides from metals of group 6 and 7 of the PSE, in particular tungsten oxide, molybdenum oxide and/or a precursor thereof, which are the active components and are deposited on at least one inorganic carrier. The most preferred metal oxide is tungsten oxide.

Preferably, the at least one inorganic carrier is selected from a group comprising silica, alumina, silica-alumina or aluminium phosphate. The inorganic carrier can contain at least about 0.1 wt % and up to 40 wt % of the active components. Amounts between 1 to 30 wt % are preferred, whereby amounts between 2 to 15 wt % are mostly preferred.

The metathesis catalyst may further comprise at least one oxide of a member of group I of the PSE or a precursor thereof as for instance comprising oxides, hydroxides, carbonates, bicarbonates, nitrates, acetates of sodium or potassium or mixtures thereof. Especially preferred are the hydroxides of sodium and potassium. The amount of these modifying compounds can be between 0.01 and 10 wt %, preferably between 0.1 and 10 wt % with respect to the metathesis catalyst.

It is further possible that the metathesis catalyst undergoes a pretreatment with at least one oxide of a member of group 1 of the PSE or a precursor thereof. For example it is preferred if silica supported tungsten oxide is used as metathesis catalyst it undergoes a pre-treatment with potassium hydroxide.

The BET surface area of the metathesis catalyst is at least >10 $m^2/g$, preferably at least >50 $m^2/g$ and mostly preferably at least ≥100 $m^2/g$.

The particle size of the metathesis catalyst depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

In another preferred embodiment said second catalyst component for double bound isomerisation of the main bed composition comprises Group 2 metal oxides, in particular magnesium oxide, calcium oxide, barium oxide, strontium oxide.

The isomerisation catalyst may also be activated for instance by heating in a flow stream of an oxygen-containing gas for about 1 to 30 hours at about 250° C. to 800° C. After calcination the isomerisation catalyst may be treated under reducing conditions as for instance with a reducing gas as hydrogen or carbon monoxide (U.S. Pat. Nos. 4,575,575; 3,546,313).

The main catalyst bed can then be prepared by admixture of the double bond isomerisation catalyst and the metathesis catalyst. The catalysts are preferably mixed in form of powders, pellets or extrudates.

The amount of the isomerisation catalyst is preferably in excess of the amount of the metathesis catalyst. However, the isomerisation catalyst can also be used in lower amounts. In an embodiment the main catalyst bed composition comprises the at least isomerisation catalyst component and the at least one metathesis catalyst component in a ratio between 5:1 and 1:1, preferably in a ratio 4:1 and 2:1, most preferably in a ratio of 3:1. It is important to note here that the weight ratio of isomerisation catalyst to metathesis catalyst does not show any influence on the overall process conversion time and yield.

The activation of the main catalyst bed is preferably carried out by heating the reactor system in an oxygen containing inert gas, like for instance nitrogen and with a reducing gas, like carbon monoxide or hydrogen (U.S. Pat. Nos. 3,915,897; 3,365,513).

The catalyst activation is preferably carried out in multiple steps. The activation can be for instance carried out according to WO 2006/052688. Typically, at first the catalyst is being oxidized for 15 to 20 minutes at a temperature between 350 and 800° C. followed by reduction for 1 to 30 hours at a temperature between 350 and 400° C., for instance in the presence of hydrogen. Subsequently, a desorption step is required for the reaction products carbon dioxide and water.

In an especially preferred embodiment said catalyst pre-bed comprises an oxide selected from the group consisting of magnesium oxide, calcium oxide, strontium oxide, barium oxide or mixtures thereof. The oxides of the pre-bed such as magnesium oxide can be used for the purification of olefin streams. This purification is based on the removal of traces of moisture, carbon dioxide and other polar compounds by adsorption. These compounds act as poisons for the catalyst when entering the reactor. Said compounds are adsorbed on the catalyst (e.g. magnesium oxide) and form acidic centres which form the source for coke formation. Subsequently, the coke covers the active sites and the catalyst is deactivated. The result of this process is a deactivation reaction which is visible as decline of the yield/conversion curve over the reaction time (tos). Thus, then using the present pre-bed the olefin streams are purified before entering the main catalyst bed.

The average BET surface of the compounds used as pre-bed is at least >10 $m^2/g$, preferably at least >50 $m^2/g$ and mostly preferably at least ≥100 $m^2/g$.

The particle size of the components of the catalyst pre-bed depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

Said catalyst pre-bed can be the same or can be different from the at least one double bond isomerisation catalyst of the main catalyst bed.

The present catalyst bed configuration is preferably used in a reactor for the conversion of at least two olefins by metathesis.

It is in particular preferred if a catalyst bed configuration comprising the at least one main catalyst bed and the at least one catalyst pre-bed in the mass ratio between 1:2 and 2.5:1, preferably between 1:1.5 and 2.5:1, more preferably between 1:1 and 2.5:1, most preferably between 1:1 and 2:1 is used for the conversion of at least two olefins by metathesis, in particular for the conversion of ethene and at least one butene (e.g. 2-butene) to propene by metathesis.

The catalyst bed is preferably part of a fixed-bed reactor. Basic types of catalytic fixed bed reactors are the adiabatic fixed-bed reactor and the isothermal fixed bed reactor. The adiabatic fixed-bed reactor is preferred for technical processes. The catalyst is usually provided in the fixed-bed reactor in form of random packings of powders, pellets or extrudates, for instance of catalytic pellets.

Typically the reactor is a packed fixed-bed reactor, which is widely used for gas solid reactions.

In an embodiment the reactor has a length to diameter ratio (l/d ratio) between 1 and 15, preferably between 1 and 10, most preferably between 1 and 5, even more preferably between 1.5 and 3.5.

The catalyst bed and the reactor are used in a process for obtaining an olefin, in particular propene, by metathesis comprising the steps of
feeding at least two olefins as starting material to a reactor, in particular a fixed bed reactor, comprising at least one catalyst bed configuration according to the invention, and
converting the at least two olefins at a pressure between 1 to 50 bar, in particular between 10 to 30 bar, at a temperature between 100 and 600° C., in particular between 250 and 500° C. to at least one new olefin by metathesis.

The metathesis reaction is preferably performed at a weight hourly space velocity (WHSV) in the range between 1 and 100 $h^{-1}$, preferably between 1 and 50 $h^{-1}$, more preferably between 1 and 10 $h^{-1}$ (the WHSV values are referring to the main catalyst bed and the fed 2-buten).

In an embodiment the one of the at least two olefins used as starting material comprises at least two carbon atoms, such as ethene, and the second of the at least two olefins used as starting material comprises at least four carbon atoms, such as a 2-butene. The mole ratio between said olefin comprising at least two carbon atoms and the olefin comprising at least four carbon atoms can be between 1 and 20, preferably 1 and 10, mostly preferably between 1 and 5.

The at least two olefins may be supplied to the reactor as a mixed stream or in form of separated streams. When using 2-butene as starting material, the butene component may be supplied as cis- or trans-2-butene or mixtures thereof. A technical 2-butene stream may contain additional small amounts of n-butane, isobutane, isobutene, 1-butene. In some embodiments the mixed C4 stream is pre-treated to increase the 2-butene content in the feed for the metathesis reaction. If a crude C4 cut from a e.g. naphtha cracker is used compounds like 1,3-butadiene, allene or acetylenes have to be removed by a selective hydrogenation step.

The olefin mixture is then contacted with the catalyst bed, whereby the olefins contact at first the catalyst pre-bed. When entering the main catalyst bed comprising the metathesis catalyst and the isomerisation catalyst, isomerisation in particular of 1-butene to 2-butene and the synthesis of propene from ethene and 2-butene occur. Besides propylene also other reaction products can be formed such as for example C5-C6 olefins.

The process may be carried out by contacting the olefins with the catalysts in the liquid phase or the gas phase depending on structure and molecular weight of the olefins used as starting material, the catalyst used and/or the reaction conditions applied such as pressure, temperatures etc. Diluents such as saturated aliphatic hydrocarbons, such as methane, ethane, propane, butane and/or inert gases like nitrogen or argon might be suitable. In any case, the presence of deactivating substances like water or oxygen should be avoided.

The metathesis catalyst is very sensitive to impurities in the feed stream. Such feed poisons are, for example, strong polar or protic compounds such as N—, O—, S— and halogen comprising compounds or carbon oxide derivatives. Typical examples are water, alcohols, ethers, ketones, aldehydes, acids, carbon dioxide, carbon monoxide, carbon oxide sulfide and the like. The consequences are reduced catalyst activity and shortened cycle times. Therefore the feed stream must be purified by passing it through suitable adsorbents before feeding to the reactor.

It is also possible to conduct the reaction in the presence of hydrogen (EP 1854776 A1).

The effluent from the metathesis reactor can be sent to a separation system for separating the product(s) from unreacted feed components. For instance, the products of the separation system may include ethene, propene, C4- and C5-compounds. The propene separated from the reaction stream is characterised by a high purity. The ethene and C4 olefins may be recycled back to the metathesis reactor or to a pre-treatment stage.

The course of the olefin conversion process in the reactor is described in the following. The reaction starts with a short activation period followed by constant propene production period. After a certain time on-stream, the catalyst continuously loses its activity. The parameter $tos_{50\%}$ characterises the time where the propene production has reached a value of 50% of the maximum conversion of n-butenes. From an industrial viewpoint, the longer this time, the higher the amount of propene produced ($n_{50\%}/(C_3H_6)$). These both characteristics are not a simple function of catalyst bed configuration, which may indicate an unknown interaction of the magnesium oxide with olefin(s) in the feed. The final behaviour of the catalyst and the impact of the size of the catalyst pre-bed cannot be described as a simple increase of the purification action. If for instance the pre-bed mass is tripled the activity is not automatically tripled. Thus, a kind of new quality is achieved by increasing the amounts of the catalyst pre-bed, i.e. increasing the amount of magnesium oxide in the pre-bed. This effect causes an increase of the produced propene amount between two consecutive regeneration steps by a reduction of the deactivation rate.

BRIEF DESCRIPTION OF THE DRAWING

The present invention is further explained in more detail by the means of the following examples with reference to the FIGURE. It shows:

FIG. 1 a diagram illustrating the time-on-stream propylene yield in ethene-2-butene metathesis for a first embodiment of the reactor bed composition according to the invention.

DETAILED DESCRIPTION OF THE INVENTION

Example 1: Catalyst Preparation

The $WO_x/SiO_2$ catalyst was prepared according to U.S. Pat. No. 4,575,575, example 1, catalyst component C. Commercial magnesium oxide powder was used, which was pelletized and crushed to receive the necessary particle size.

Example 2: Catalytic Testing of a First Reactor Bed Composition

Catalytic tests were performed in a tubular (4 mm i.d.) continuous-flow fixed-bed reactor made of quartz at 1.4 bar and 300° C. using a $C_2H_4$:trans-2-$C_4H_8$:$N_2$=64.3:25.7:10 feed. $C_2H_4$ (Linde, purity >99.95%), trans-2-$C_4H_8$ (Linde, purity >99.0%) were extra purified with molsieve 3 A, while "oxysorb" (Resteck) and molsieve 3A were applied for purifying $N_2$ (Air Liquide, purity >99.999%). The main catalyst is a physical mixture of MgO (0.3-0.7 mm) and $WO_x/SiO_2$ (0.3-0.7 mm) with a weight ratio of 3.0 MgO (0.3-0.7 mm) was additionally used as a pre-bed arranged upstream. Both beds were placed within the isothermal zone of the reactor. The reactor is heated by an electrical furnace, which is located inside a box preheated to 120° C. Up- and downstream lines to the reactor are also inside this box. The amounts of the main catalyst and the pre-bed were in the Standard bed configuration 258 and 129 mg, respectively. The total gas flow was 14.9 ml (STP)·min$^{-1}$ yielding a WHSV (weight hourly space velocity) of 1.9 h$^{-1}$ related to trans-2-$C_4H_8$.

Before catalytic testing, the following pre-treatment was performed. The reactor was heated in a flow of pure nitrogen up to 400° C. with a heating rate of 5 K·min$^{-1}$. The temperature was held constant for 2 h. Hereafter, an air flow was fed to the reactor followed by temperature rising to 525° C. with a heating rate of 5 K·min$^{-1}$. After 2 hours in this flow at the final temperature, the reactor was cooled to 400° C. (2 K·min$^{-1}$) in a flow of pure nitrogen. The temperature was held constant for 0.5 h followed by feeding an $H_2$:$N_2$=30:70 (mol/mol) flow for 0.5 h. Then, the reactor was flushed with a flow of pure nitrogen and heated in the same flow up to 550° C. with a heating rate of 5 K·min$^{-1}$. The temperature was held constant for 16 h. Finally, the reactor was cooled down to 300° C., where the metathesis reaction was studied.

The diagram of FIG. 1 shows the time-on-stream propylene yield in ethylene-2-butene metathesis over 75 mg $MgO_{pre-bed}$ and 300 mg of MgO:($WO_x/SiO_2$)=3/1 (●) and over 129 mg $MgO_{pre-bed}$ and 258 mg of MgO:($WO_x/SiO_2$)=3/1 (○) at 300° C. The catalyst fillings have practically the same volume. Feed composition: trans-2-$C_4H_8$/$C_2H_4$/$N_2$=26/64/10, WHSV: 1.9 h$^{-1}$.

The propene yield was calculated according the equation 1:

$$Y_{C_3H_6} = S_{C_3H_6} \times X_{n-butenes} \qquad (1),$$

where $S_{C_3H_6}$ is propene selectivity calculated according to $$S_{C_3H_6} = \frac{m_{C_3H_6}^{outlet}}{m_{C_3H_6}^{outlet} + \sum m_{C_5}^{outlet} + \sum m_{C_6}^{outlet}}, \qquad (2)$$

where $m^{outlet}$ is mass flow of $C_3H_6$, $C_5$ and $C_6$ olefins, respectively $X_{n-butenes}$ is conversion of n-butenes, calculated according to $$X_{n-butenes} = \left(1 - \frac{X_{t-2-C_4H_8}^{outlet} + X_{1-C_4H_8}^{outlet} + X_{cis-2-C_4H_8}^{outlet}}{X_{t-2-C_4H_8}^{inlet}}\right) \qquad (3)$$

where $x_i^{inlet}$ and $x_i^{outlet}$ represent mole fractions of 1- or 2-butenes at the reactor inlet and outlet, respectively.

Example 3: Catalytic Testing of a Second Reactor Bed Composition

The test was carried out as described in Example 2. The pre-bed contained 204 mg MgO and the main-bed 200 mg of the MgO:($WO_3/SiO_2$)=3:1 mixture.

Example 4: Catalytic Testing of a Third Reactor Bed Composition

The test was carried out as described in Example 2. The pre-bed contained 249 mg MgO and the main-bed 165 mg of the MgO:($WO_3/SiO_2$)=3:1 mixture.

Example 5: Catalytic Testing of a Fourth Reactor Bed Composition

The test was carried out as described in Example 2. The pre-bed contained 304 mg MgO and the main-bed 129 mg of the MgO:($WO_3/SiO_2$)=3:1 mixture.

Example 6: Comparative Example

The test was carried out as described in Example 2. The pre-bed contained 75 mg MgO and the main-bed 300 mg of the MgO:($WO_3/SiO_2$)=3:1 mixture.

The results of the catalytic tests are summarised in Table 1.

TABLE 1

Reactor filling and selected catalytic results.

| Example | pre-bed/ mg | main bed/mg | Ratio | tos$_{50\%}$/h | n$_{50\%}$(C$_3$H$_6$)*/ mol |
|---|---|---|---|---|---|
| 2 | 129 | 258 | 0.50 (1:2) | 171 | 2.72 |
| 3 | 204 | 200 | 1.02 (1:1) | 174 | 2.68 |
| 4 | 249 | 165 | 1.51 (1.5:1) | 174 | 2.47 |
| 5 | 304 | 122 | 2.49 (2.5:1) | 169 | 2.02 |
| 6 | 75 | 300 | 0.25 (1:4) | 123 | 1.91 | tos$_{50\%}$: time required for losing 50% of n-butenes conversion
n$_{50\%}$: amount of propene produced at tos50%
Main bed is a physical mixture of MgO and $WO_x/SiO_2$ (MgO:($WO_x/SiO_2$) = 3/1)
Pre-bed is $MgO_{pre-bed}$.
Ratio is expressed as $MgO_{pre-bed}$:(MgO:($WO_x/SiO_2$) = 3/1).
The catalyst bed (pre-bed plus main bed) volume in all examples is constant.

The results in table 1 clearly indicate that an increased pre-bed to main bed-ratio improves the catalyst performance in the embodiment of the invention.

Example 7

The catalyst in example 3 was regenerated after approximately 200 h on metathesis stream. The regeneration conditions are summarised in table 2.

| Regeneration steps | $T_{start}$/ °C. | $T_{end}$/ °C. | Heating rate/ °C./min | Holding time at $T_{end}$/h |
|---|---|---|---|---|
| Purge with $N_2$ | 300 | 300 | | 0.5 |
| Start of oxidation in $N_2/O_2 = 99:1$ | | 300 | | 2 |
| Increase temperature to 360° C. | 300 | 360 | 1 | 0.5 |
| Increase temperature to 420° C. | 360 | 420 | 1 | 0.5 |
| Step-up oxygen to $N_2/O_2 = 97:3$ | 420 | 420 | | 2 |
| Increase temperature to 480° C. | 420 | 480 | 1 | 0.5 |
| Step-up oxygen to $N_2/O_2 = 94:6$ | 480 | 480 | | 2 |
| Increase temperature to 525° C. | 480 | 525 | 1 | 0.5 |
| Step-up oxygen to $N_2/O_2 = 79:21$ (air) | | 525 | | 3 |
| Cooling down in $N_2$ | 525 | 400 | 2 | 0.5 |
| Reduction in $N_2/H_2 = 70/30$ | | 400 | | 0.5 |
| Purge with $N_2$ | | 400 | | 0.5 |
| Desorption in $N_2$ | 400 | 550 | 5 | 16 |
| Cooling down in $N_2$ | 550 | 300 | | |

The next propene production cycle was started after the last cooling step. The production and regeneration cycles were repeated. The results of the $8^{th}$ and $9^{th}$ cycle are summarised in table 3.

TABLE 3

Formed propene over reactor filling with ratio $MgO_{pre\text{-}bed}:(MgO:(WO_x/SiO_2)) = 1.02$ during consecutively performed metathesis/regeneration cycles

| Cycle No. | $n(C_3H_6)$/mol during period of 145 h on stream |
|---|---|
| 8 | 2.56 |
| 9 | 2.52 |

The results in table 3 demonstrate that the improved catalyst performance as result of the optimised pre-bed to main-bed mass ratio is retained over 9 regeneration/production cycles.

The invention claimed is:

1. A catalyst bed configuration for conversion of ethene and n-butene to propene comprising
at least one main catalyst bed comprising
   a) at least one first catalyst component comprising a metathesis catalyst, and
   b) at least one second catalyst component comprising a catalyst for double bond isomerisation, whereby the first and second catalyst are admixed with each other, and
at least one catalyst pre-bed arranged upstream of the at least one main catalyst bed consisting of at least one compound selected from the group of alkaline earth oxides,
wherein
the mass ratio of the at least one catalyst pre-bed and the at least one main catalyst bed is between 1:2 and 1.5:1, wherein a mass ratio of 1:1.6 of catalyst pre-bed and main catalyst bed in case of magnesium oxide as catalyst pre-bed and a mixture of magnesium oxide and tungsten oxide on a silica carrier in a ratio of 7:1 as main catalyst bed for the disproportion of pentene is disclaimed.

2. The catalyst bed configuration according to claim 1, wherein the main catalyst bed comprises the at least one isomerisation catalyst component and the at least one metathesis catalyst component in a ratio between 5:1 and 1:1.

3. The catalyst bed configuration according to claim 1, wherein the metathesis catalyst comprises oxides of metals of the $6^{th}$ and $7^{th}$ group of the PSE deposited on at least one inorganic carrier.

4. The catalyst bed configuration according to claim 1, wherein said second catalyst component for double bond isomerisation of the main catalyst bed comprises Group 2 metal oxides.

5. The catalyst bed configuration according to claim 1, wherein said catalyst pre-bed comprises an oxide selected from the group consisting of magnesium oxide, calcium oxide, strontium oxide, barium oxide or mixtures thereof.

6. The catalyst bed configuration according to claim 1, wherein the main catalyst bed comprises the at least one isomerisation catalyst component and the at least one metathesis catalyst component in a ratio of 3:1.

7. The catalyst bed configuration according to claim 1, wherein the metathesis catalyst comprises tungsten oxide, molybdenum oxide, and/or a precursor thereof deposited on at least one inorganic carrier.

8. The catalyst bed configuration according to claim 1, wherein said second catalyst component for double bond isomerisation of the main catalyst bed comprises magnesium oxide, calcium oxide, barium oxide, strontium oxide or mixtures thereof.

9. A catalyst bed configuration for conversion of ethene and n-butene to propene comprising
at least one main catalyst bed comprising
   a) at least one first catalyst component comprising a metathesis catalyst, and
   b) at least one second catalyst component comprising a catalyst for double bond isomerisation, whereby the first and second catalyst are admixed with each other, and
at least one catalyst pre-bed arranged upstream of the at least one main catalyst bed consisting of at least one compound selected from the group of alkaline earth oxides,
wherein
the mass ratio of the at least one catalyst pre-bed and the at least one main catalyst bed is between 1:1.5 and 1.5:1.

10. A process for making propene comprising:
feeding ethene and n-butene as a starting material to a reactor comprising at least one catalyst bed configuration according to claim 1; and
reacting the starting material in the reactor at a pressure between 1 to 50 bar at a temperature between 100 and 600° C. to isomerize n-butene to 2-butene and to metathesize ethene and 2-butene to make propene.

11. The process according to claim 10, wherein the ratio between ethene and n-butene is between 1 to 20.

12. The process according to claim 10, wherein the metathesis reaction is performed at a weight hourly space velocity (WHSV) in the range between 1 and 100 $h^{-1}$.

13. The process according to claim 10, wherein the reactor is a fixed bed reactor.

14. The process according to claim 10, wherein the ethene and n-butene are converted to propene by metathesis at a pressure between 10 to 30 bar, at a temperature between 250 to 500° C.

15. The process according to claim 10, wherein the ratio between ethene and n-butene is between 1 to 5.

16. A process for making propene from at least ethene and n-butene, comprising:
feeding a starting material comprising ethene and n-butene to a reactor comprising:

at least one catalyst bed configuration comprising:
  at least one main catalyst bed comprising:
    a) at least one first catalyst component comprising a metathesis catalyst, and
    b) at least one second catalyst component comprising a catalyst for double bond isomerisation, whereby the first and second catalyst components are admixed with each other,
  at least one catalyst pre-bed arranged upstream of the at least one main catalyst bed consisting of at least one alkaline earth oxide,
  wherein a mass ratio of the at least one catalyst pre-bed and the at least one main catalyst bed is between 1:2 and 1.5:1; and
reacting the starting material in the reactor, at a pressure between 1 bar to 50 bar and at a temperature between 100° C. and 600° C., to isomerize n-butene to 2-butene and to metathesize ethene and 2-butene to make propene.

\* \* \* \* \*